United States Patent [19]

Watanabe

[11] Patent Number: 5,022,396

[45] Date of Patent: *Jun. 11, 1991

[54] CATHETER FOR SIMULTANEOUSLY MEASURING MONOPHASIC ACTION POTENTIAL AND ENDOCARDIAC CAVITY PRESSURE

[76] Inventor: Hideto Watanabe, No. 6-21, Nishinagaehonmachi, Toyama-shi, Toyama-ken, Japan

[*] Notice: The portion of the term of this patent subsequent to May 8, 2007 has been disclaimed.

[21] Appl. No.: 448,921

[22] Filed: Dec. 12, 1989

[30] Foreign Application Priority Data

Dec. 19, 1988 [JP] Japan ................... 63-163543[U]

[51] Int. Cl.⁵ .................. A61B 5/0402; A61N 1/05
[52] U.S. Cl. ............................. 128/642; 128/673; 128/786
[58] Field of Search ........ 128/642, 673, 675, 784–786, 128/419 P

[56] References Cited

U.S. PATENT DOCUMENTS

| | | | |
|---|---|---|---|
| 4,600,017 | 7/1986 | Schroppel | 128/675 X |
| 4,682,603 | 7/1987 | Franz | 128/642 |
| 4,690,155 | 9/1987 | Hess | 128/642 |
| 4,922,912 | 5/1990 | Watanabe | . |

*Primary Examiner*—Lee S. Cohen
*Attorney, Agent, or Firm*—Hoffmann & Baron

[57] ABSTRACT

A catheter capable of simultaneously measuring the action potential of myocardiac cells by means of a pair of electrodes, and the endocardiac cavity pressure by means of a pressure transducer. One electrode is provided to the enclosing front surface of a catheter body when the catheter body is brought into contact with the endocardiac surface guided into the endocardiac cavity. The other electrode is provided to the distal peripheral surface of the catheter body and is disposed within the endocardiac cavity when the catheter is guided into the endocardiac cavity and the other electrode contacts the endocardiac surface. The pressure transducer is provided to the peripheral surface of the distal section, for measuring the endocardiac cavity pressure and outputting it in the form of an electrical pressure signal. Lead wires are connected to the pair of electrodes and the pressure transducer, and are guided from the rear section of the catheter body in order to transfer the measured action potential and electrical pressure signals, from the catheter body, to processing and display equipment.

2 Claims, 1 Drawing Sheet

(PRIOR ART)

CATHETER FOR SIMULTANEOUSLY MEASURING MONOPHASIC ACTION POTENTIAL AND ENDOCARDIAC CAVITY PRESSURE

FIELD OF THE INVENTION

The present invention relates generally to a MAP (Monophasic Action Potential) catheter adapted to be inserted into an endocardiac cavity for the purpose of measuring the action potential of the myocardiac cells in the endocardium, by means of a pair of electrodes. More particularly, the present invention relates to such a MAP catheter which is also adapted to simultaneously detect the pressure within the endocardiac cavity while measuring the action potential of the myocardiac cells.

DESCRIPTION OF PRIOR ART

Hitherto, a variety of prior art MAP catheters are known.

One such prior art MAP catheter is shown in FIG. 3 and disclosed generally in U.S. Pat. No. 4,682,603 to Franz. As illustrated in FIG. 3, this prior art MAP catheter has two electrodes 1 and 3. Electrode 1 formed from Ag-AgC1 wire mass, partly protrudes from the distal section of the catheter body, whereas the other electrode 3, also formed from Ag-AgC1 wire mass, is exposed by a hole 2b drilled through the peripheral surface 2a in the distal section, and cemented therein by cement 4. However, while this catheter can measure the action potential of myocardiac cells, it nevertheless suffers from several shortcomings and drawbacks.

In particular, in the MAP catheter of the type generally shown in FIG. 3 and disclosed in U.S. Pat. No. 4,682,603, Ag, which is expensive, must be used in sufficient amounts to form electrode masses 1 and 3. Also, in such a MAP catheter, there exists the problem that the hole 2b in the peripheral surface 2a of the distal section may become clogged with foreign matter, causing a poor contact between blood and the electrodes when within the cardiac cavity.

U.S. Pat. No. 4,690,155 to Hess discloses a MAP catheter in which the distal tip electrode and lateral surface electrode are both disposed within the distal tip compartment which is secured to the elongated tubular body. The distal tip compartment is separated into two electrically-isolated or insulated compartments, referred to as the distal tip compartment and proximal compartment, each of which is filled with a material that has electrically conductive properties. This electrically conductive filler material is in electrical connection with lead wires to form the distal tip electrode and lateral surface electrode, respectively, within the respective insulated compartments. As disclosed, the electrically conductive filler material functions as electrodes which are brought into contact with the endocardium and the cardiac cavity, respectively. Each of these electrodes have associated contact surfaces which are substantially flat, and may also be somewhat convex or somewhat concave depending on particular contact requirements. While the catheter disclosed in U.S. Pat. No. 4,690,155 is capable of measuring action potentials, it nevertheless suffers from several shortcomings and drawbacks.

In particular, with contact electrodes of such a catheter being made from electrically conductive filler material, it is very difficult to obtain sufficient electrical conductivity with the endocardium and cardiac cavity, so as to be capable of detecting the MAP waveform with a high degree of sensitivity. In addition, the contact electrodes of such a catheter being formed from such electrically conductive filler material, results in a broader contact surface with the endocardium and cardiac cavity, thereby resulting in an undesired increase in the polarization voltage.

The present applicant has disclosed in U.S. application Ser. No. 07/252,856, now U.S. Pat. No. 4,922,912 a MAP catheter having pair of electrodes formed from Ag-AgC1 wires. Such Ag-AgC1 wires are made to protrude intact from the front surface and the peripheral surface in the distal section of the catheter body, respectively. However, while such a catheter overcomes many of the shortcomings and drawbacks of prior art MAP catheters, it nevertheless is impossible to measure with such a catheter, the endocardiac cavity pressure which is known to be diagnostically significant information.

While it is possible to measure the endocardiac cavity pressure using a specially designated catheter having a pressure transducer, it has not been recognized or appreciated by those skilled in the art, that by simultaneously measuring both the action potential of the endocardiac surface and the pressure within endocardiac cavity, very significant diagnostic results and interrelationships can be obtained, thereby providing clinically useful data regarding a patient's health.

Moreover, it has never occurred to anyone that the action potential and the endocardiac cavity pressure are positively interrelated. Consequently, no one has ever disclosed, taught or suggested providing a single catheter capable for simultaneously measuring the action potential and endocardiac cavity pressure within a patient's heart.

SUMMARY OF THE INVENTION

Accordingly, it is a primary object of the invention to provide a single catheter having a pressure transducer capable of simultaneously and reliably measuring the action potential of the myocardiac cells and the endocardiac cavity pressure so that it will be possible for the first time, to accurately probe and determine in a diagnostic sense, the very significant interrelationship between the electrophysiological function and the mechanical function of the heart, and its relation to a patient's health.

In accordance with the present invention, a single catheter is provided for simultaneously measuring action potentials of myocardiac cells and endocardiac cavity pressure in a heart. In general, the catheter comprises a catheter body, first and second electrodes, a pressure transducer, and lead wires. The catheter body is designed for guided insertion into the endocardiac cavity and for being brought into contact with an endocardiac surface having myocardiac cells. The catheter body includes a distal section and a rear section, and the distal section has a front-end enclosing surface and a peripheral surface. The first electrode is provided to the front enclosing surface, whereas a second electrode is provided to the peripheral surface. The first and second electrodes are disposed in the distal section of the catheter body so that when the catheter body is guided into the endocardiac cavity, the first electrode is brought into contact with an endocardiac surface, and the second electrode is disposed in the endocardiac cavity. The pressure transducer is disposed in the peripheral surface of the catheter body and is capable of measuring the endocardiac cavity pressure when the catheter body is disposed within the endocardiac cavity. Also, the pressure transducer produces as output, an electrical pressure signal corresponding to the measured endocardiac cavity pressure. Further, the lead wires are connected to the first electrode, second electrode and pressure transducer respectively, and extend out from the rear section of the catheter body, so as to transfer the measured action potential and electrical pressure signals outwardly from the rear section of the catheter body.

According to the present invention, the catheter is inserted into the endocardiac cavity. The first electrode provided to the front-end surface in the distal section of the catheter body is brought into contact with the endocardiac surface. The second electrode provided to the peripheral surface in the distal section, is situated in the endocardiac cavity. This causes the action potential to be derived from the second electrode, while the endocardiac cavity pressure is measured by the pressure transducer in the catheter body, situated by itself in the endocardiac cavity.

In accordance with the present invention, the correlation between the two detected signals relating to monophasic action potential and endocardiac cavity pressure, enables the interrelationship between the electrophysiological function (i.e. action potential) and the mechanical function (i.e. pressure) to be determined. Furthermore, since the relative positions of the electrodes are fixed, measurement with high reliability is made possible with the catheter of the present invention. It is expected that as a result of the catheter of the present invention, clinical applications to cardiopathy will become more active.

In another embodiment of the present invention, the addition of electrodes for pacing enables a MAP measurement with high accuracy in the pacing state when using only a single catheter of the present invention.

Since the electrode for MAP measurement is made from Ag-AgCl wires which protrude intact from respective surfaces of the distal portion of the catheter body, the amount of Ag that must be used, is saved, and also, the myocardiac action potential can be measured with high sensitivity and high fidelity since the polarization voltage generated between the endocardiac surface and electrodes hereof is extremely small. Further, since the preferred embodiment of the present invention, the end of each electrode is needle-like pointed type, the problem of foreign matter adhering to the surface of the electrodes is avoided.

BRIEF DESCRIPTION OF THE DRAWINGS

For a further understanding of the objects of the present invention, reference is made to the following detailed description of the preferred embodiment which is to be taken in connection with the accompanying drawings, wherein.

DESCRIPTION OF THE PREFERRED EMBODIMENTS

Figure 1:
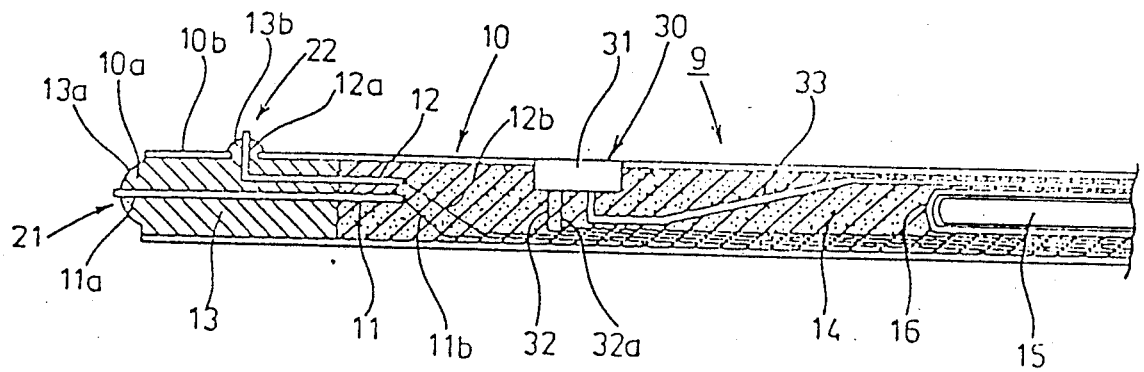
FIG. 1 is a cross-sectional view of an essential portion of the catheter in accordance with one embodiment of the present invention.

Referring to illustrated FIG. 1, there is shown a MAP catheter 9 having a pressure transducer in accordance with the first embodiment of the present invention. In the first embodiment, the MAP catheter comprises a catheter body 10 having a diameter of, for example, 2 mm. Preferably, the catheter body 10 consists of a tube made of a plastic material such as vinyl chloride or polyurethane. An Ag-AgCl wire (i.e. line) 11 consisting of an Ag line plated with AgCl and having a diameter of, for example, 0.3 meters, projects about 0.5 mm from the central position of the front end surface 10a, and functions as the first electrode having a needle-like geometry. An Ag-AgCl wire (i.e. line) 12 also projects about 0.05 mm from a hole provided in the peripheral surface 10b, and functions as the second electrode of the catheter hereof having a needle-like geometry, as well. Notably, the hole in peripheral surface 10b is formed, for example, about 5 mm proximal from the end surface 10a, in a direction perpendicular to that of the Ag-AgCl line 11. The distal section of the catheter body 10 is filled with epoxy cement 13 to secure the Ag-AgCl lines 11 and 12 in position and to form a catheter closing section. The sections 11a and 11b of the Ag-AgCl lines 11 and 12 respectively, project outwardly and are completely sealed in order to prevent blood from entering the catheter body 10. The projecting sections 11a and 12a of the Ag-AgCl lines 11 and 12, are surrounded by an approximately semispherical epoxy cement portions 13a and 13b, respectively, thus forming a pair of electrodes 21 and 22.

The Ag-AgCl lines 11 and 12 are guided from the portion of the filled epoxy cement 13, and are connected midway to lead wires 11b and 12b, respectively, embedded in an elastic material 14 such as silicone rubber. The lead wires 11b and 12b extend within the distal section towards and through the rear section, and are then guided away from the extreme portion rear section (not shown) of the catheter body 10, so as to be capable of connection to the input of an appropriate device (not shown) for processing and display of signals sent along these lead wires.

As shown in FIG. 1, there is mounted below the surface of the catheter body 10, a conventional pressure transducer 30 having a pressure receiving surface 31 for measuring the endocardiac cavity pressure. Placement of the pressure transducer 30 within the catheter body surface is such that the pressure receiving surface 31 is positioned at, for example, 25 mm from the front surface 10a in the distal section. The pressure receiving surface 31 is aligned with a second hole forwarding the peripheral surface 10b in the distal section, and is left exposed for purposes of sensing the pressure in the endocardiac cavity while simultaneously measuring action potential in the endocardiac cavity. Lead wires 32 and 32a are provided for receiving electrical detection signals produced from the pressure transducer 30, whereas a tube 33 is provided for introducing air to the pressure transducer 30, for use as a reference pressure. The lead wires 32 and 32a and tube 33 are embedded is the elastic material 14, extend from the distal section to the rear section of the catheter body 10, and are then guided away from the extreme portion rear section (not shown) of the catheter body 10, into a processing and display device (not shown).

Notably, FIG. 1 only shows the front essential portion of the catheter body 10 which has an overall length of about 1 to 1.5 meters. The silicon rubber 14 is provided behind the portion of the distal section which is filled with epoxy cement 13, and extends over a length of 30 mm, for example. A sheath 16 for inserting a guide wire 15 into the rear portion of the catheter body 10, is inserted from behind and extends up to this silicon rubber section 14.

The MAP catheter 9 thus constructed is guided within a blood vessel by the guide wire 15, and eventually inserted into the cardiac cavity. Particularly, the semispherical configuration of the portion 13a surrounding the electrode 21 enables the slightly exposed portion of the projecting section 11a to be positively guided over, and brought into contact with, the endocardium. Since the electrode 22 is also provided with a semispherical surrounding portion 13b, the catheter 9 can be smoothingly guided into the cardiac cavity without the cardiac cavity suffering any damage. When set in position inside the cardiac cavity, the exposed portion of the projecting section 12a of the side electrode 22 protrudes beyond the peripheral surface 10b of the catheter body 10, so that, unlike the conventional electrode 3 in FIG. 3, there is no danger of foreign matter adhering thereto. Accordingly, the electrode 22 is positively brought into contact with the blood. Also, since the silicon rubber section 14 is provided between the guide wire 15 and the epoxy cement section 13, the pressure exerted by the guide wire 15 through the sheath 16 is diminished or "softened," which ensures operational safety.

When the catheter body 10 is installed within the cardiac cavity in such a manner, the action potential is detected by the pair of electrodes 21 and 22. Therewhile, the pressure transducer 30 is "fixed" at the position of the optimum portion of the endocardiac cavity (i.e. by using electrodes 21 and 22 as a reference), and this ideal positioning of the pressure transducer 30 within the cardiac cavity, thereby enables the endocardiac cavity pressure to be detected with an extremely high degree of reliability.

The action potential signal (at the measurement point) supplied from the lead wires 11b and 12b, and the endocardiac cavity pressure signal supplied from lead wires 32 and 32a, are both guided away from the extreme portion (not shown) of the rear section of the catheter body and are both amplified at an output device and monitored on a CRT screen. Preferably, both the action potential and endocardiac cavity pressure waveforms are displayed on a common time axis in order that they may be analyzed and compared.

As a result of the present invention, the electrophysiological function and the mechanical function of a heart can be directly compared and studied in a quantitative as well as qualitative sense. When necessary, the comparison can be recorded on recording paper and arithmetic operations can be performed on these two detected waveforms.

Figure 2:
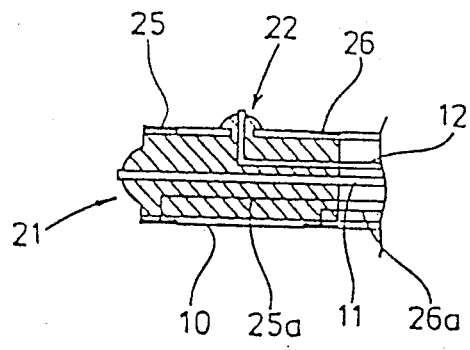
FIG. 2 is a cross-sectional view of an essential portion of the catheter in accordance with the other embodiment of the present invention.

FIG. 2 illustrates a second embodiment of the present invention. In FIG. 2, the components which are identical with those in FIG. 1 have the same reference characters.

In FIG. 2, only the front end portion of the catheter 9 of FIG. 1 is shown. In this particular embodiment, annular-shaped pacing electrodes 25 and 26 made of stainless steel or platinum having a width, e.g., 1 mm, are embedded within the surface of the distal section of the catheter body 10. These annular-shaped pacing electrodes are embedded within the surface of the catheter body 10 so as to form a continuous surface therewith. For this purpose, portions to the annular-shaped pacing electrodes are cut away from the catheter body 10. Inside the catheter body 10, the pacing electrodes 25 and 26 are connected to lead wires 25a and 26a respectively, which extend outwardly from the rear end of the catheter body 10 so that they may be connected to pacing apparatus (not shown) well known in the art. With such modifications to the catheter of FIG. 1, a MAP catheter with a pressure transducer and pacing electrodes is thusly provided.

This makes it possible to measure the MAP and the endocardiac cavity pressure with one catheter while pacing and sensing are being done as needed. In other words, when the heart rate is under control, local myocardiac active states can be monitored accurately while they are being interrelated from the aspects of the mechanical phenomena and the electrophysiological phenomena of the heart.

In the above described embodiments, the semispherical surrounding portions 13a and 13b of the Ag-AgCl lines may be dispensed within some instances, and desired results can be obtained without them.

In other embodiments of the present invention, the front end enclosing surface of the catheter body 10 may be formed as a closed section which is in one piece with the catheter body proper, with the non-projecting section of the Ag-AgCl line 12 being embedded in the tube surface itself of the catheter body 10. The semispherical surrounding portions 13a and 13b may then be formed in one piece with the distal end section positioning the Ag-AgCl lines and the elastic body. For the elastic body provided behind the catheter closing section, other materials may be employed. The annular configuration of the pacing electrodes ensures positive contact with the endocardium. However, the electrodes may, in some cases, simply have a pointed configuration.

Furthermore, the pressure transducer and/or pacing electrodes can be applied to the catheter in accordance with the present invention, wherein the guide wire 15 in FIG. 1 is dispensed with altogether, and the catheter body 10 is operated directly by manual operation. Alternatively, woven Dacron ® material can be inserted as a flexible material in place of the guide wire 15.

Figure 3:
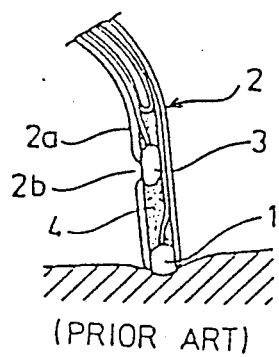
FIG. 3 is a cross-sectional view of an essential portion of a conventional catheter.

In addition, the pressure transducer and/or pacing electrodes may be applied to the conventional MAP catheter shown in FIG. 3 in accordance with the principles of the present invention. In such an embodiment, the pressure transducer can be placed in the back of the element 3.

While the particular embodiments shown and described above have been proven to be useful is many applications involving the bio-medical instrumentation art, further modifications of the present invention herein disclosed will occur to the skilled in the art to which the present invention pertains, and all such modifications are deemed to be within the scope and spirit of the present defined by the following claims.

What is claimed is:

1. A catheter for simultaneously measuring action potentials of myocardiac cells and endocardiac cavity pressure in a heart, said catheter comprising:

a catheter body for guided insertion into said endocardiac cavity and being brought into contact with an endocardiac surface having myocardiac cells, said catheter body including a distal section and a rear section, said distal section having a front enclosing surface and a peripheral surface;

first and second electrodes, said first electrode being provided to said front enclosing surface and said second electrode being provided to said peripheral surface, said first and second electrodes being disposed in said distal section of said catheter body so that when said catheter body is guided into said endocardiac cavity, said first electrode is brought into contact with an endocardiac surface, and said second electrode is disposed in said endocardiac cavity;

a pressure transducer disposed in said peripheral surface of said distal section of said catheter body and being capable of measuring said endocardiac cavity pressure when said catheter body is disposed within said endocardiac cavity, and producing as output an electrical pressure signal corresponding to said measured endocardiac cavity pressure;

lead wires connected to said first electrode, second electrode and pressure transducer respectively, and extending out from said rear section of said catheter body, so as to transfer said measured action potential and electrical pressure signals outwardly from said rear section of said catheter body;

a pair of pacing electrodes provided to said peripheral surface of said distal section of said catheter body; and pacing lead wires connected to said pacing electrodes in said catheter body and extending out from said rear section of said catheter body.

2. The catheter of claim 1, wherein said first and second electrodes for measuring the action potential, comprise:

Ag-AgCl wires protruding from said front enclosing surface and said peripheral surface, respectively, of said distal section of said catheter body.

* * * * *